(12) United States Patent
Hirano et al.

(10) Patent No.: US 8,353,822 B2
(45) Date of Patent: Jan. 15, 2013

(54) MOLDED ELASTOMER FOR ENDOSCOPE

(75) Inventors: Yuko Hirano, Machida (JP); Mitsuhiro Nakamura, Hachioji (JP); Akinobu Nakano, Hachioji (JP); Hirokazu Kamioka, Fussa (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 0 days.

(21) Appl. No.: 13/238,523

(22) Filed: Sep. 21, 2011

(65) Prior Publication Data

US 2012/0077920 A1    Mar. 29, 2012

Related U.S. Application Data

(63) Continuation of application No. PCT/JP2011/058625, filed on Apr. 5, 2011.

(30) Foreign Application Priority Data

Apr. 8, 2010  (JP) .................. 2010-089789

(51) Int. Cl.
*A61B 1/00*  (2006.01)

(52) U.S. Cl. ........ 600/133; 600/140; 600/139; 600/153; 600/144; 524/545; 524/430

(58) Field of Classification Search .................. 600/133, 600/140, 139, 144, 153; 524/430, 545
See application file for complete search history.

(56) References Cited

FOREIGN PATENT DOCUMENTS

| JP | 3-122153 | | 5/1991 |
|---|---|---|---|
| JP | 3122153 A | * | 5/1991 |
| JP | 2005-245517 | | 9/2005 |
| JP | 2005-245517 A | * | 9/2005 |
| JP | 2006-218106 | | 8/2006 |
| JP | 2006-218106 A | * | 8/2006 |
| JP | 2006-330727 | | 12/2006 |
| JP | 2006-330727 A | * | 12/2006 |
| JP | 2007-211233 | | 8/2007 |
| JP | 2007-306946 | | 11/2007 |
| JP | 2007-306946 A | * | 11/2007 |
| WO | WO 2009/013945 A1 | | 1/2009 |

* cited by examiner

*Primary Examiner* — Robert D. Harlan
(74) *Attorney, Agent, or Firm* — Scully, Scott, Murphy & Presser, P.C.

(57) ABSTRACT

A molded elastomer for an endoscope is provided, which includes a fluorine-containing elastomer and a filler. The filler includes thermal black in a content of 1 to 10 parts by mass based on 100 parts by mass of the fluorine-containing elastomer, and plate alumina in a content of 2 to 10 parts by mass based on 100 parts by mass of the fluorine-containing elastomer.

12 Claims, 1 Drawing Sheet

MOLDED ELASTOMER FOR ENDOSCOPE

CROSS-REFERENCE TO RELATED APPLICATIONS

This is a Continuation Application of PCT Application No. PCT/JP2011/058625, filed Apr. 5, 2011, which will be published under PCT Article 21(2) in Japanese.

This application is based upon and claims the benefit of priority from the prior Japanese Patent Application No. 2010-089789 filed Apr. 8, 2010, the entire contents of which are incorporated herein by reference.

BACKGROUND OF THE INVENTION

1. Field of the Invention

The present invention relates to a molded elastomer for an endoscope.

2. Description of the Related Art

In endoscopes, a molded elastomer containing a fluorine-containing elastomer with excellent chemical resistance is used as an outer cover for a curved tube used therein. Such a molded elastomer may be, for example, a rubber tube for a curving section, which is molded by cross-linking a kneaded mixture containing prescribed starting materials. The starting materials used may include, for example, a ternary copolymer of vinylidene fluoride/hexafluoropropylene/tetrafluoroethylene, a liquid fluorine-containing elastomer, perhexa 2,5B, triallyl isocyanate, hydrated silica, and reinforcing carbon.

It is required to be completely disinfected and sterilized for medical endoscopes, and recently a new disinfecting and sterilizing method has come into use. According to the method, chemical liquid which turns into water or harmless substance after the treatment, i.e., which is non-polluting and gives no environmental destruction is used. Specifically, hydrogen peroxide plasma, peracetic acid, acidic water, or the like is used. An autoclave method which is performed under high temperatures and high pressure may be also mentioned.

The disinfection or sterilization is performed under severe conditions of very strong oxidizability, and thus parts of an endoscope are problematically corroded. Even a molded article which uses a fluorine-containing elastomer with excellent chemical resistance, conventionally, may cause faults such as cracks and swelling, if it is exposed to the severe conditions for a long time. If it is attempted to avoid faults such as cracks and swelling, problems such as occurrence of outgas are raised, and elasticity which is specific to an elastomer may be sometimes impaired. Such an elastomer cannot be used for the endoscope.

For example, JP-A 2005-245517 (KOKAI) proposes molded articles for enhancing resistances under a severe disinfection or sterilization environment. In this publication, two or more kinds of cross-linkable fluorine-containing elastomers are used, and carbon is mixed therewith as a filler. Further, JP-A 2007-211233 (KOKAI) proposes that when a fluorine-containing elastic copolymer is cross-linked, alumina is mixed therewith as a reinforcing agent.

As an outer cover for a curved tube in an endoscope is very thin, if the outer cover is cut or pin holes are formed therein, the endoscope fails due to water leakage. It is required, accordingly, to have physical resistances in addition to the chemical resistance described above for the outer cover for the curved tube in the endoscope. It is desired that the physical resistances are maintained even after the severe disinfection or sterilization is performed. An outer cover for the curved tube in the endoscope having all of the conditions described above has not been obtained yet.

BRIEF SUMMARY OF THE INVENTION

According to one embodiment, a molded elastomer for endoscope includes a fluorine-containing elastomer and a filler, the filler including thermal black in an content of 1 to 10 parts by mass based on 100 parts by mass of the fluorine-containing elastomer, and plate alumina in an content of 2 to 10 parts by mass based on 100 parts by mass of the fluorine-containing elastomer.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
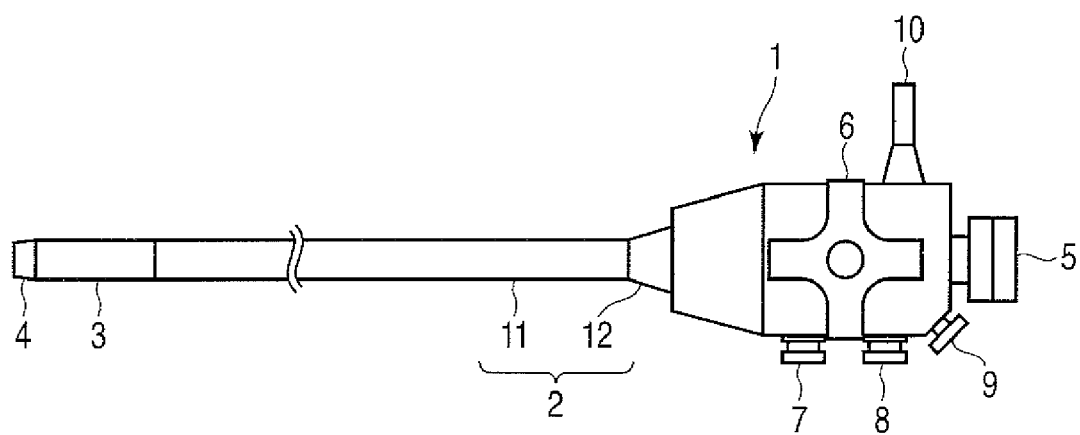
FIG. 1 is a schematic side view showing an endoscope which uses a molded elastomer according to an embodiment.

A molded elastomer for an endoscope according to an embodiment of the present invention will be explained below.

The molded elastomer for an endoscope according to the embodiment comprises a fluorine-containing elastomer and a filler. Ternary copolymers are preferably used as the fluorine-containing elastomer, and it may include, for example, vinylidene fluoride/hexafluoropropylene/tetrafluoroethylene ternary copolymers. The ternary copolymer can be expressed by the following general formula, and has excellent chemical resistance.

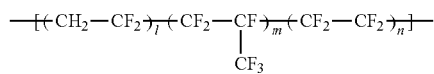

wherein l, m and n are each an integer.

The filler to be added to the fluorine-containing elastomer contains a prescribed amount of thermal black and a prescribed amount of plate alumina.

The thermal black provides reinforcement to the molded elastomer, and is contained in an amount of 1 to 10 parts by mass based on 100 parts by mass of the fluorine-containing elastomer. When the content of the thermal black is less than 1 part by mass, resistance to perforation is reduced due to insufficient reinforcement. On the other hand, when the content of the thermal black is more than 10 parts by mass, the reinforcement becomes too large, and thus a modulus becomes large.

The thermal black has preferably physical properties of a specific gravity of 1.6 to 2.0, an average particle size of 400 to 600 μm, and a surface area of 5 to 7 m²/g. The content of the thermal black is preferably from 2 to 8 parts by mass based on 100 parts by mass of the fluorine-containing elastomer.

On the other hand, the plate alumina has an effect of enhancing impact resistance of the molded elastomer, and is contained in an amount of 2 to 10 parts by mass based on 100 parts by mass of the fluorine-containing elastomer. When the content of the plate alumina is less than 2 parts by mass, the impact resistance cannot be secured, and thus tear strength and the resistance to perforation are reduced. On the other hand, if the content of the plate alumina is more than 10 parts by mass, fluidity is reduced, the modulus is increased, and the appearance becomes poor.

As needle-shaped alumina cannot secure the desired impact resistance, the resistance to perforation is reduced. In this embodiment, accordingly, the alumina which forms the filler in combination with the thermal black is limited to the plate alumina.

The plate alumina has preferably physical properties of an average particle size of 1 to 20 μm, an average thickness of 0.06 to 0.36 μm, an aspect ratio of 45 to 80, and a specific surface area of 3 to 10 m$^2$/g. The content of the plate alumina is preferably from 3 to 8 parts by mass based on 100 parts by mass of the fluorine-containing elastomer. It should be noted that the average particle size of the plate alumina refers to a 50% particle size according to laser diffraction.

In addition to the components described above, silica may be further contained as a reinforcing agent. When the silica is contained, resistance to cutting and the resistance to perforation are further enhanced. When 3 to 15 parts by mass of the silica is contained based on 100 parts by mass of the fluorine-containing elastomer, the desired effects can be obtained with no disadvantages.

The silica is not particularly limited, and it has preferably a specific gravity of about 2.4 to 2.8, and a volume average particle size of about 1 to 10 μm.

As a colorant, channel black may be contained. When 5 parts by mass or less of the channel black is contained based on 100 parts by mass of the fluorine-containing elastomer, the desired coloring effect can be obtained with no disadvantages such as reduced fluidity. In some cases, the molded elastomer can be made to have a desired hardness by the addition of the channel black.

When the channel black is used, it is desired to adequately adjust the total amount of the thermal black and the channel black to 6 parts by mass or less based on 100 parts by mass of the fluorine-containing elastomer.

The channel black has preferably physical properties of a specific gravity of 1.6 to 2.0, an average particle size of 15 to 40 μm, and a surface area of 40 to 200 m$^2$/g.

Additives added to the fluorine-containing molded elastomer of this embodiment are as follows:

As a plasticizer, for example, a low molecular weight fluorine-containing elastomer having no cross-linking reactive group may be used.

The content of the plasticizer is preferably from 1 to 50 parts by mass based on 100 parts by mass of the fluorine-containing elastomer. When it is contained in such a content, functions of the plasticizer can sufficiently be expressed, and moldability is also good. In addition, surface stickiness such as blooming does not occur. The content of the plasticizer is more preferably from 1 to 15 parts by mass based on 100 parts by mass of the fluorine-containing elastomer.

As a cross-linking agent, for example, peroxides, which are said to have good chemical resistance, may be used. Specifically, examples thereof may include dicumyl peroxide, di-t-butylperoxydiisopropyl benzene, and 2,5-dimethyl-2,5-di(t-butylperoxy)hexane and the like. Of these, 2,5-dimethyl-2,5-di(t-butylperoxy)hexane is particularly preferable.

The content of the cross-linking agent is preferably from 0.5 to 5 parts by mass, based on 100 parts by mass of the fluorine-containing elastomer, more preferably 0.5 to 2 parts by mass.

A cross-linking aid may include, for example, triallyl isocyanurate, triallyl cyanurate, triallyl trimellitate, N,N'-m-phenylene dimaleimide, trimethylolpropane trimethacrylate, and the like. In addition, acrylate monomers, methacrylate monomers, and the like may be used. Of these, triallyl isocyanurate is particularly preferable.

The content of the cross-linking aid is preferably from 1 to 10 parts by mass, based on 100 parts by mass of the fluorine-containing elastomer, more preferably 2 to 6 parts by mass.

When the amounts of the cross-linking agent and the cross-linking aid are too small, the cross-linking insufficiently occurs, and therefore the mechanical properties of the molded article, such as hardness and tensile strength tend to be insufficient. On the other hand, when the amounts of the cross-linking agent and the cross-linking aid are too large, failures such as occurrence of outgas, and occurrence of blooming or a phenomenon in which orientation components bleed to the surface, generally-called a bleed, tend to be caused.

The fluorine-containing molded elastomer of this embodiment can be produced by various common methods. First, the fluorine-containing elastomer of the ternary copolymer as a main component and the prescribed filler are masticated in a kneading machine such as a twin roller, a kneader or a Banbury mixer, and then various kinds of the additives are added thereto. For example, when a cross-linking reaction is performed with a cross-linking agent, the cross-linking aid and the filler are added while it is kneaded, and finally the plasticizer is added to prepare a molding material.

The obtained molding material can be molded in a known method for molding rubber such as an injection molding, an extrusion molding or a transfer molding. For example, after the molding material is filled in a mold having a desired shape and it is hot-pressed, for example, radiation is applied thereto. If desired, secondary cross-linking may be performed in a thermal air current.

The shape of the molded article is not particularly limited, and an appropriate shape may be selected from a sheet, a bar, a ring and various complicated blocks depending on the application thereof.

The molded elastomer for an endoscope of this embodiment can be formed into, for example, an outer cover for a bend in an endoscope, a member for preventing bending of an endoscope, a switch button of an endoscope or an outer cover which covers the switch button, or an O-ring which is used inside an endoscope.

Referring to the drawings, embodiments will be explained in more detail below. In each drawing, the same reference numerals are given to the same or similar constituent elements, and overlapping explanations are omitted.

Figure 2:
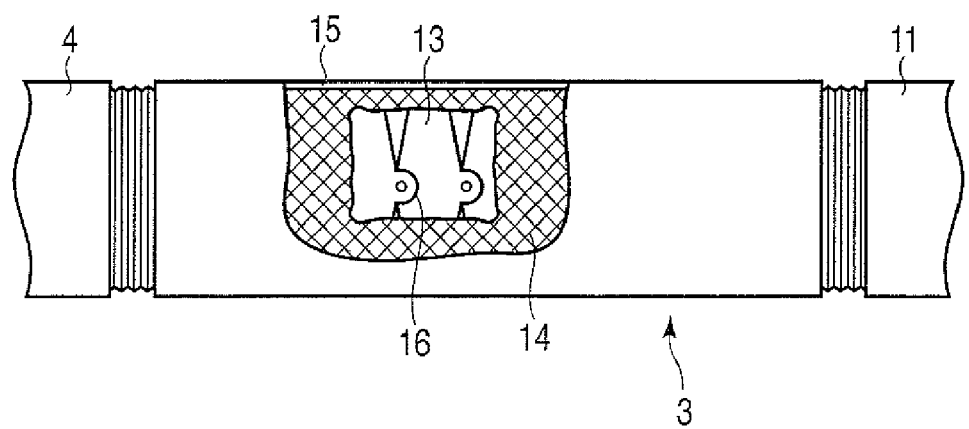
FIG. 2 is an enlarged side view of a part of the endoscope shown in FIG. 1.

FIG. 1 is the schematic side view of the endoscope according to one embodiment of the present invention. FIG. 2 is the enlarged side view of a part of the endoscope shown in FIG. 1. It should be noted that in FIG. 2, a curving section is drawn with a partial cutaway.

The endoscope shown in FIG. 1 comprises an operation body 1, a flexible section 2, a curving section 3, and a tip section 4. The flexible section 2 extends from the operation body 1, and is bent by applying external force. The curving section 3 is supported at one end by the tip of the flexible section 2, and is curved to form any angle by operations prescribed in the operation body 1. The tip section 4 is another end of the curving section 3. The tip section 4, the curving section 3 and the flexible section 2 form an insertion section which is inserted into a lumen when the endoscope is used.

The operation body 1 comprises an eyepiece section 5, an operation knob 6, a button 7 for sending air and water, a button 8 for suction, a port 9 for inserting a treatment tool, and a corrugated tube 10 for introducing light. The eyepiece section 5 enables to observe an object to be observed which is located at the front of the tip section 4 through an objective lens (not shown in FIGS.) provided on the tip section 4 and optical fibers (not shown in FIGS.) inserted in the curving section 3 and the flexible section 2. The operation knob 6 controls a curvature of the curving section 3, and whereby the tip section 4 can be turned to a desired direction.

The button 7 for sending air and water is provided for controlling air and water sent from the port for sending air and water provided on the tip section 4, and the button 8 for suction is provided for controlling the suction from a suction port provided on the tip section 4. The port 9 for inserting a treatment tool enables to use a treatment tool (not shown in FIGS.) such as a clamp by inserting the tool therethrough and protruding the tool from the tip section 4. The corrugated tube 10 for introducing light leads light from an external light source, and has the optical fibers (not shown in FIGS.) which irradiate the light to the object to be observed which is located at the front of the tip section 4 in the inside thereof.

The flexible section 2 has optical fibers (not shown in FIGS.) for observation and lighting in the inside thereof, and further has a flexible tube 11, a member 12 for preventing bending, and the like. The member 12 for preventing bending prevents the bending of the flexible tube 11 at a position where the tube 11 is connected to the operation body 4, and comprises an elastic body containing an elastomer.

The curving section 3 has a plurality of bending pieces 13 having optical fibers (not shown in FIGS.) in the inside, a network tube 14 which covers the bending pieces 13, an outer cover 15 which covers the network tube 14, and the like. Each of the bending pieces 13 has an almost cylindrical shape, and the adjacent pieces are connected to each other through a connecting pin 16 as a rotating axis in a freely rotatable manner. These bending pieces 13 are connected to a wire which is not shown in FIGS. As the curving section 3 has such a structure, it can be curved to form a desired angle.

The network tube 14 which covers the bending pieces 13 is, for example, formed by knitting metal thin wires, and prevents damage of the outer cover 15 which is caused by the rotation of the bending pieces 13. The outer cover 15 comprises an elastic body containing an elastomer, and prevents damage of an inner wall caused by the curving section 3 when, for example, the insertion section is put into and out from the lumen and the curving operation is performed in the lumen.

The tip section 4 has, as stated above, the object lens, the port for sending air and water, the suction port, channels, and the like. The object lens is utilized for observing the object to be observed which is located at the front of the tip section 4, and also utilized for irradiating illumination light to the object to be observed. The port for sending air and water is formed, for example, as a nozzle which sprays fluid to the surface of the object lens, and in this case, the suction port is utilized for removing liquid remaining on the surface of the object lens.

In such an endoscope, in order to prevent leakage of liquid and gas caused by an air and water sending or suction operation, O-rings (not shown in FIGS.) are used in junctions between components forming these paths. In addition, in order to prevent corrosion of the components of this endoscope in the disinfection or sterilization treatment, the button 7 for sending air and water and the button 8 for suction may be covered with an outer cover (not shown in FIGS.) comprising an elastic body.

In the endoscope shown in FIGS, at least one of the outer cover 15 of the curving section 3, the member 12 for preventing bending, the O-rings, the button 7 for sending air and water, the button 8 for suction, and outer covers which cover these buttons 7 and 8 are substantially formed from the fluorine-containing molded elastomer which is molded by cross-linking reaction of the molding material comprising the fluorine-containing elastomer and the filler.

Even if the fluorine-containing molded elastomer of this embodiment has a thickness such as 0.1 to 1 mm, it has excellent physical resistances. Specifically the tear strength is 25 kN/m or more, and the 100% modulus is 2.8 MPa or less. Moreover, it is difficult to form pinholes, and the hardness is adequate. Such properties are not substantially impaired even after a sterilization treatment in severe conditions. For example, even after a high pressure steam sterilization is repeatedly performed under conditions of 115° C.×30 minutes, 121° C.×20 minutes, or 136° C.×30 minutes, the properties can be maintained at 90% or more of those before the sterilization.

As described above, in this embodiment, the combination of the thermal black and the plate alumina is selected as the filler in the molded elastomer for an endoscope comprising the fluorine-containing elastomer and the filler. Further, the content of the thermal black is defined as 1 to 10 parts by mass based on 100 parts by mass of the fluorine-containing elastomer, and the content of the plate alumina is defined as 2 to 10 parts by mass based on 100 parts by mass of the fluorine-containing elastomer.

As the specific filler is contained, the molded article of this embodiment has high physical resistances which are not reduced even if the disinfection and sterilization treatment is performed under severe conditions. Moreover, the molded article of this embodiment has sufficient resistance to a high pressure steam sterilization treatment.

Example

Examples of the present invention will be explained below, but the invention is not limited by Examples.

A Material having the following composition was prepared.

| | |
|---|---|
| a fluorine-containing elastomer (a fluorine-containing rubber ternary copolymer) | 100 parts by mass |
| a plasticizer (liquid fluorine-containing rubber) | 10 parts by mass |
| a cross-linking agent (an organic peroxide) | 0.7 part by mass |
| a cross-linking aid (triallyl isocyanurate) | 2 parts by mass |

In addition, thermal black and plate alumina, which are shown below, were added in combination to the material described above as the filler. The contents here are all based on 100 parts by mass of the fluorine-containing elastomer.

| | |
|---|---|
| thermal black (carbon black) (a specific gravity of 1.8; an average particle size of 500 μm; a surface area of 6 m²/g) | 1 part by mass |
| plate alumina (alumina) (an average particle size of 5 μm; an average thickness of 0.07 μm) | 5 parts by mass |

The materials described above were kneaded in an open roll to give a compound as the molding material.

The compound was filled in a mold, and cross-linking molding was performed at 160° C. for 10 minutes. After that, secondary cross-linking was performed in an oven at 200° C.

for 4 hours to obtain a molded article in the state of a tube. The molded article had a wall thickness of about 0.5 mm. This was referred to as No. 1.

In addition, molded articles Nos. 2 to 13 were obtained in the same manner as in No. 1 except that the contents of the thermal black and the plate alumina, which were used as the filler, were changed to contents shown in Table 1 below. Furthermore, a molded article No. 14 was obtained in the same manner as in No. 3 except that the plate alumina was changed to 5 parts by mass of needle-shaped alumina.

TABLE 1

| No. | Thermal black (part by mass) | Plate alumina (part by mass) |
| --- | --- | --- |
| 1 | 1 | 5 |
| 2 | 10 | 5 |
| 3 | 5 | 2 |
| 4 | 5 | 10 |
| 5 | 2 | 5 |
| 6 | 8 | 5 |
| 7 | 5 | 3 |
| 8 | 5 | 8 |
| 9 | 5 | 5 |
| 10 | 0.5 | 5 |
| 11 | 15 | 5 |
| 12 | 5 | 1 |
| 13 | 5 | 15 |

A tear strength, a 100% modulus, a perforation strength and a hardness were determined for the obtained molded articles.

The tear strength was measured in accordance with JIS K 6252 [a tear test]. A test piece had an angle-shaped, a test speed was set at 500 mm/minute, and the maximum strength thereof was measured. It is required that the tear strength is 25 (kN/m) or more.

The 100% modulus was obtained in a usual manner. It is required that the 100% modulus is 2.8 MPa or less.

In order to determine the perforation strength, a test piece having a thickness of 0.5 mm, and a pin having a diameter of 1.5 mm at the tip were prepared. The pin had a mass of 50 g. After the pin was dropped to the test piece from a prescribed height, the test piece was pressurized from one side of the test piece with air at 0.5 kgf/cm$^2$, and whether air was leaked or not was determined. When the air leakage was not confirmed, the pin was dropped from a higher position than the previous one, and the same measurement was performed.

The maximum dropping height (mm) of the pin at which the air leakage did not occur was measured, and the height was used as an indicator of the perforation strength. When the dropping height is 80 mm or higher, it is evaluated that the perforation strength is good, and reaches an acceptable level.

The hardness was obtained in accordance with JIS K 6253. It is required that the hardness is less than 70 Shore A.

The obtained results are summarized in Table 2 below, together with the tear strength, the 100% modulus, the perforation strength and the overall judgment.

TABLE 2

| No. | Tear strength (kN/m) | 100% modulus (MPa) | Perforation strength (mm) | Hardness (shore A) | Overall judgment |
| --- | --- | --- | --- | --- | --- |
| 1 | 39 | 2.4 | 80 | 59 | Δ |
| 2 | 35 | 2.7 | 100 | 62 | Δ |
| 3 | 32 | 2.2 | 80 | 61 | Δ |
| 4 | 40 | 2.8 | 120 | 61 | Δ |
| 5 | 39 | 2.7 | 80 | 60 | Δ |
| 6 | 30 | 2.4 | 90 | 61 | ○ |
| 7 | 25 | 2.3 | 80 | 58 | Δ |
| 8 | 37 | 2.7 | 110 | 61 | Δ |
| 9 | 35 | 2.3 | 110 | 60 | ◎ |
| 10 | 37 | 2.2 | 70 | 57 | X |
| 11 | 48 | 7 | 120 | 70 | X |
| 12 | 20 | 2.3 | 70 | 58 | X |
| 13 | 54 | 5 | 130 | 66 | X |
| 14 | 33 | 2.3 | 70 | 60 | X |

As shown in above Table 2, when 1 to 10 parts by mass of the thermal black and 2 to 10 parts by mass of the plate alumina are contained (Nos. 1 to 9), all of the tear strength, the 100% modulus, the perforation strength and the hardness reach the acceptable levels.

On the contrary, when the condition of the content of the thermal black, the content of the plate alumina or the shape of the alumina is insufficient (Nos. 10 to 14), the desired property could not be obtained. Specifically, No. 10 in which the content of the thermal black is too low cannot obtain the enough perforation strength, and it was 70 mm. No. 11 in which the content of the thermal black is too high has a large 100% modulus of 7 MPa. Moreover the molded article No. 11 has a high hardness of 70 Shore A.

No. 12 in which the content of the plate alumina is too low has a low tear strength of 20 kN/m, and a perforation strength of only 70 mm. No. 13 in which the content of the plate alumina is too high has a large 100% modulus of 5 MPa. When the alumina is in the state of a needle, even if the prescribed amount of the alumina is contained together with the prescribed amount of the thermal black, enough perforation strength cannot be secured. The results of No. 14 show that when alumina other than the plate alumina is contained together with the thermal black in the prescribed amounts, the perforation strength is at the highest at 70 mm.

When even any one of the tear strength, the 100% modulus, the perforation strength and the hardness departs from the defined range, the overall judgment is NG. That is, it was confirmed that such a molded article could not attain the object of the present invention.

The molded articles Nos. 1 to 9 were subjected to a treatment, 100 times, in which they were treated with steam having a temperature of 135° C. under a pressure of 233 kPa (2.3 atm.) for 30 minutes in an autoclave apparatus. The physical properties of the tear strength, the 100% modulus, the perforation strength and the hardness were examined for the molded articles which were subjected to the autoclave treatment in the same manner as above. It was confirmed that the physical properties of the molded articles Nos. 1 to 9 were not reduced even after the autoclave treatment, and all of the retentions were 90% or higher.

A steam permeability of the molded article No. 9 was examined in accordance with JIS Z 0208 before and after the autoclave treatment. The steam permeability was $4.0 \times 10^{-4}$ (g/24 hrs·m$^2$·mmHg/cm) or less before the autoclave treatment, and 90% or higher of the value could be retained even after the treatment.

In addition, as shown in Table 3 below, molded articles Nos. 15 to 18 were obtained in the same manner as in No. 1 except that silica which is the reinforcing agent, or channel black which is the colorant was concurrently used. Contents shown in Table 3 are parts by mass based on 100 parts by mass of the fluorine-containing elastomer.

TABLE 3

| No. | Thermal black (parts by mass) | Plate alumina (parts by mass) | Silica (parts by mass) | Channel black (parts by mass) |
|---|---|---|---|---|
| 15 | 5 | 5 | 3 | 0 |
| 16 | 5 | 5 | 10 | 0 |
| 17 | 5 | 5 | 15 | 0 |
| 18 | 2.5 | 5 | 10 | 2.5 |

The tear strength, the 100% modulus, the perforation strength, and the hardness were examined for the obtained molded article in the same manner as above. The obtained results are summarized in Table 4 below together with the overall judgment.

TABLE 4

| No. | Tear strength (kN/m) | 100% modulus (MPa) | Perforation strength (mm) | Hardness (shore A) | Overall judgment |
|---|---|---|---|---|---|
| 15 | 33 | 2.2 | 90 | 60 | ○ |
| 16 | 35 | 2.3 | 110 | 60 | ◎ |
| 17 | 37 | 2.5 | 100 | 62 | Δ |
| 18 | 35 | 2.3 | 110 | 60 | ○ |

The molded articles Nos. 15 to 18 were subjected to an autoclave treatment under the same conditions as described above, and the physical properties thereof were examined in the same manner as above after the treatment. As a result, it was confirmed that the physical properties of the molded article Nos. 15 to 18 were not reduced after the autoclave treatment, and 90% or higher of the values were retained.

A steam permeability of the molded article No. 18 was examined in the same manner as described above before and after the autoclave treatment. The steam permeability was $4.0 \times 10^{-4}$ (g/24 hrs·m²·mmHg/cm) or lower before the autoclave treatment, and 90% or higher value could be retained even after the treatment.

As explained above, when the prescribed amount of the thermal black and the prescribed amount of the plate alumina are contained, a molded elastomer which is excellent in all of the properties of the tear strength, the 100% modulus, the perforation strength and the hardness can be obtained. Such properties are hardly deteriorated even after the autoclave treatment, and it was confirmed that a retention of 90% or higher could be obtained.

The present invention is not limited to Examples described above, and various modifications can be carried out without departing from the gist of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A molded elastomer for an endoscope comprising:
a fluorine-containing elastomer and a filler, the filler comprising thermal black in a content of 1 to 10 parts by mass based on 100 parts by mass of the fluorine-containing elastomer, and plate alumina in a content of 2 to 10 parts by mass based on 100 parts by mass of the fluorine-containing elastomer,
wherein the molded elastomer has a tear strength of 25 kN/m or more and a 100% modulus of 2.8 MPa or less.

2. The molded elastomer for an endoscope according to claim 1, wherein the alumina has 50% particle size according to laser diffraction of 1 to 20 :m, an average thickness of 0.06 to 0.36 :m, an aspect ratio of 45 to 80, and a specific surface area of 3 to 10 m²/g.

3. The molded elastomer for an endoscope according to claim 1, further comprising silica in a content of 3 to 15 parts by mass based on 100 parts by mass of the fluorine-containing elastomer.

4. The molded elastomer for an endoscope according claim 1, wherein the content of the thermal black is 2 to 8 parts by mass based on 100 parts by mass of the fluorine-containing elastomer.

5. The molded elastomer for an endoscope according to claim 1, wherein the content of the plate alumina is 3 to 8 parts by mass based on 100 parts by mass of the fluorine-containing elastomer.

6. The molded elastomer for an endoscope according to claim 1, further comprising channel black in a content of 5 parts by mass or less based on 100 parts by mass of the fluorine-containing elastomer.

7. An endoscope device comprising an insertion section having a curving section which is covered with a molded elastomer as an outer cover, the molded elastomer comprising:
a fluorine-containing elastomer and a filler, the filler comprising thermal black in a content of 1 to 10 parts by mass based on 100 parts by mass of the fluorine-containing elastomer, and plate alumina in a content of 2 to 10 parts by mass based on 100 parts by mass of the fluorine-containing elastomer, the molded elastomer having a tear strength of 25 kN/m or more and a 100% modulus of 2.8 MPa or less.

8. The endoscope according to claim 7, wherein the alumina has 50% particle size according to laser diffraction of 1 to 20 μm, an average thickness of 0.06 to 0.36 μm, an aspect ratio of 45 to 80, and a specific surface area of 3 to 10 m²/g.

9. The endoscope according to claim 7, further wherein the molded elastomer further comprises silica in a content of 3 to 15 parts by mass based on 100 parts by mass of the fluorine-containing elastomer.

10. The endoscope according to claim 7, wherein the content of the thermal black is 2 to 8 parts by mass based on 100 parts by mass of the fluorine-containing elastomer.

11. The endoscope according to claim 7, wherein the content of the plate alumina is 3 to 8 parts by mass based on 100 parts by mass of the fluorine-containing elastomer.

12. The endoscope according to claim 7, wherein the molded elastomer further comprises channel black in a content of 5 parts by mass or less based on 100 parts by mass of the fluorine-containing elastomer.

* * * * *